United States Patent [19]

Goulding

[11] Patent Number: 5,325,861

[45] Date of Patent: Jul. 5, 1994

[54] METHOD AND APPARATUS FOR MEASURING A PARAMETER OF A GAS IN ISOLATION FROM GAS PRESSURE FLUCTUATIONS

[75] Inventor: Peter P. Goulding, Oceanside, Calif.

[73] Assignee: Puritan-Bennett Corporation, Carlsbad, Calif.

[21] Appl. No.: 980,551

[22] Filed: Nov. 23, 1992

Related U.S. Application Data

[63] Continuation-in-part of Ser. No. 725,723, Jul. 8, 1991, abandoned, which is a continuation-in-part of Ser. No. 336,688, Apr. 12, 1989, abandoned.

[51] Int. Cl.$^5$ .............................................. A61B 5/08
[52] U.S. Cl. ................................ 128/719; 128/204.21; 73/863.83; 73/863.03; 73/23.3
[58] Field of Search ..................... 128/716–719, 128/725, 730, 202.22, 204.21–204.24, DIG. 10; 137/803–805, 814, 826, 833; 73/863, 23.2, 23.21, 23.3, 31.05, 863.01–863.03, 863.81, 863.83, 436; 417/540

[56] References Cited

U.S. PATENT DOCUMENTS

| | | |
|---|---|---|
| 2,437,446 | 3/1948 | Stephens . |
| 3,548,849 | 12/1970 | Purcell . |
| 3,747,628 | 7/1973 | Holster . |
| 3,777,344 | 12/1973 | Glass . |
| 3,826,284 | 7/1974 | Broker . |
| 3,942,558 | 3/1976 | Honda et al. . |
| 4,202,352 | 5/1980 | Osborn .................... 128/719 |
| 4,631,966 | 12/1986 | Brugnoli ................ 63/863.03 |
| 4,799,374 | 1/1989 | Bosssart ..................... 73/1 G |
| 4,874,016 | 10/1989 | Tseng ........................ 137/826 |
| 5,050,615 | 9/1991 | Malkamäki ................. 128/719 |

FOREIGN PATENT DOCUMENTS

0006256A1 6/1979 European Pat. Off. .
1556791 9/1977 United Kingdom .

Primary Examiner—Edgard S. Burr
Assistant Examiner—Eric P. Raciti
Attorney, Agent, or Firm—Fulwider Patton Lee & Utecht

[57] ABSTRACT

In measuring a selected parameter of a test gas in isolation from gas pressure fluctuations, a pump draws the test gas through a storage capacitor into a sensor, storing the gas in the storage capacitor. A valve closes a fluid flow path which admits the test gas to the storage capacitor and opens a fluid flow path between the storage capacitor and a constant pressure alternate gas source, isolating the storage capacitor and the sensor from pressure fluctuations in the test gas. The storage capacitor prevents any mixing of the test gas with the alternate gas until measurement of the selected parameter has been accomplished.

14 Claims, 3 Drawing Sheets

METHOD AND APPARATUS FOR MEASURING A PARAMETER OF A GAS IN ISOLATION FROM GAS PRESSURE FLUCTUATIONS

RELATED APPLICATIONS

This application is a continuation-in part of co-pending application Ser. No. 07/725,723, filed Jul. 8, 1991, now abandoned which was a continuation-in-part of Ser. No. 07/336,688, filed Apr. 12, 1989 now abandoned.

BACKGROUND OF THE INVENTION

FIELD OF THE INVENTION

The present invention relates generally to the measurement of parameters of gases. The invention more particularly relates to a method and apparatus for measuring a selected parameter of a gas at a substantially constant desired pressure, in isolation from fluctuations in the pressure of the gas, for use with gas sensors having a substantially linear measurement response to the selected parameter in a desired pressure range, and having a substantially non-linear measurement response to the selected parameter outside the desired pressure range.

DESCRIPTION OF RELATED ART

There are numerous instances in which a parameter of a gas must be measured. For example, in the medical field it is often necessary to measure such parameters as oxygen and carbon dioxide concentrations in a gas mixture in either an inspiration or an expiration line of a patient ventilator. Fluctuations in the pressure of the gas during the measurement process can affect the accuracy of the measurements or even render performance of the measurements impossible. Such fluctuations in pressure of a test gas can be caused by pressure fluctuations in the patient airway, or by pressure waves and vibrations from pump devices or other elements in the gas sensing equipment itself. Carbon dioxide sensors are typically affected linearly by changes in pressure of the test gas, allowing for some degree of pressure compensation and correction of measurements taken with the carbon dioxide sensors. However, oxygen sensors are typically only linearly affected by changes in pressure within a given pressure range, typically below a threshold pressure particular to the individual type of oxygen sensor, above which the measurement response of the sensor can change in a non-linear and uncharacterizable manner. Even with pressure compensation of carbon dioxide concentration of a test gas, various kinds of calibration, time delay and interpolation errors can occur when pressure fluctuations of the test gas is allowed to occur. Therefore, it is highly desirable to minimize pressure fluctuations in the test gas as much as possible, and maintain the pressure of the test gas relatively constant at a desired pressure while the measurements are being performed.

If the gas is not in motion, it is relatively easy to keep the pressure constant so as to carry out the necessary measurements. Even if the gas is in motion, if the pressure of the moving gas remains relatively constant, the concentration measurements can be performed satisfactorily. However if the gas flow rate and pressure are not uniform, as is the case in an airway of a patient respirator, accurate parameter measurements, particularly for measurement of oxygen concentrations, can become difficult or impossible, and fluctuations have thus been a common source of error in measurement of oxygen and carbon dioxide gas concentrations with conventional gas sensor systems.

Recent advances in medical diagnostic and therapeutic procedures have created a need for a way to continuously monitor parameters of the gases being inhaled or exhaled by a patient on a respirator. Various methods of measuring such parameters have been proposed, but none of them has adequately solved the problem of making accurate measurements under the conditions of fluctuating pressure and flow rate which are encountered in respirator airways. Therefore, there remains a need for a way to measure parameters of a gas such as a gas in a patient airway in isolation from fluctuations in the pressure and flow rate of the gas.

SUMMARY OF THE INVENTION

The present invention provides a method and apparatus for measuring a parameter of a test gas in isolation from fluctuations in the pressure and flow rate of the gas by drawing the gas into a storage capacitor and then admitting an alternative gas at a constant pressure to an inlet of the capacitor while the measurement is being performed.

Briefly and in general terms, apparatus according to the invention includes a sensor to measure a selected parameter of a test gas supplied from a source of the test gas, a constant pressure alternate gas source, a storage capacitor connected in fluid communication with the source of test gas and the alternate gas source upstream from the sensor for storing a quantity of the gas, a dual chamber pressure damping capacitor connected in fluid communication with the sensor downstream from the sensor, a pump downstream from the sensor connected in fluid communication with the dual chamber damping capacitor for drawing the gas into the sensor, and fluid flow control means for controlling flow of the test gas and alternate gas.

According to the invention, the fluid flow control means opens a first fluid flow path for the test gas into the storage capacitor for a sufficient time to enable the pump to draw the gas through the storage capacitor into the sensor and thereby to fill the storage capacitor with the test gas. Thereafter, the first flow path is closed and a second flow path between the storage capacitor and the constant pressure alternate gas source is opened, thereby isolating the storage capacitor and the sensor from any fluctuations in the pressure of the test gas. The storage capacitor prevents any substantial mixing of the alternate gas with the stored test gas for a sufficient time to enable the sensor to measure the selected parameter of the test gas under constant pressure conditions. The pressure isolation provided by the storage capacitor permits the test gas to flow continuously through the sensor during the measurement process while preventing pressure fluctuations from interfering with accuracy of the measurement.

In a preferred embodiment of the invention, the fluid flow control means comprises a valve, such as a solenoid valve, having a first inlet in fluid communication with a source of the test gas, a second inlet in fluid communication with the alternate gas source and an outlet in fluid communication with the storage capacitor. The valve opens the first flow path by connecting the outlet to the first inlet and opens the second flow path by connecting the outlet to the second inlet.

The fluid flow control means preferably also includes timing control means such as a microprocessor or the like which selectively applies power to the solenoid valve to control the flow of gases into the storage capacitor. The microprocessor also controls an output display or the like to ensure that the sensor output is provided only during the time that the pressure of the test gas in the sensor is being held constant. In a preferred embodiment, the test gas comprises an inspired gas in an airway of a patient respirator. The alternate gas source preferably comprises the ambient atmosphere.

In a preferred embodiment, the storage capacitor of the invention comprises an elongated chamber characterized by a length-to-diameter ratio much larger than unity; for example, a chamber having a length of about 75 centimeters and a diameter of about 0.5 centimeter has been found to give satisfactory results. The storage capacitor can be fabricated, for example, by forming an elongated channel which establishes a fluid flow path in a block of material. The dual chamber pressure damping capacitor also preferably includes first and second cavities connected by an intermediate elongated constrictor channel establishing a resistor fluid flow path between the two cavities, and the constrictor channel also preferably has a length-to-diameter ratio much larger than unity. The cavities and the constrictor channel may also be advantageously formed a block of material. In a presently preferred embodiment, the storage capacitor block and the dual chamber pressure damping capacitor are joined together to form a pneumatic block.

According to the invention, a method of measuring a selected parameter of a test gas in isolation from gas pressure fluctuations is provided that utilizes the apparatus described above. The method comprises the steps of opening a first fluid flow path for the test gas into a storage capacitor; drawing the test gas through the storage capacitor and into a sensor for measurement of the selected parameter, thereby filling the storage capacitor with the test gas; closing the first fluid flow path; opening a second fluid flow path between a constant pressure alternate gas source and the storage capacitor and thereby isolating the sensor from any fluctuations in the pressure of the test gas; and measuring the selected parameter of the test gas under substantially constant pressure conditions before any substantial mixing of the alternate gas with the test gas stored in the storage capacitor occurs. In a preferred embodiment for use in measuring a selected parameter of a mixture of inspired gases in an airway of a patient respirator, the step in the above method of opening the first fluid flow path comprises opening a fluid flow path between the airway and the storage capacitor.

From the above it may be seen that the present invention provides a system and method that enhances the accuracy and reliability of measurement of gas parameters in a patient's airway. These benefits are provided by relatively simple and robust apparatus that does not interfere with the basic function of the respirator. Other aspects and advantages of the present invention will become apparent from the following detailed description and the accompanying drawings which illustrate by way of example the features of the invention.

DETAILED DESCRIPTION OF THE PREFERRED EMBODIMENT

Figure 1:
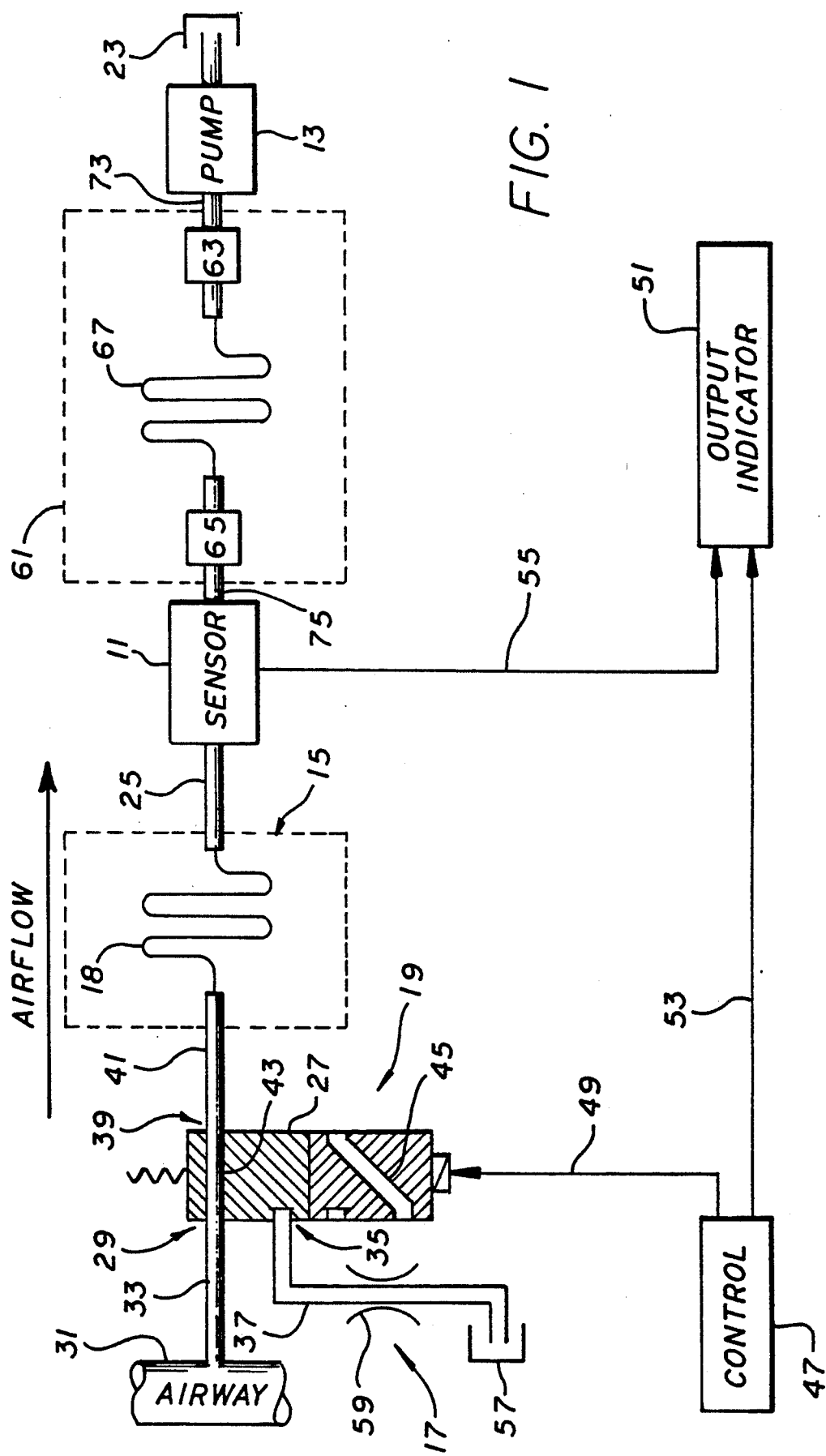
FIG. 1 is a fluid flow diagram of apparatus according to the invention for measuring a parameter of a gas in isolation from pressure fluctuations.

As is shown in the drawings, which are included for purposes of illustration, the invention is embodied in a novel method and apparatus for measuring a parameter of a gas in isolation from fluctuations in the pressure of a gas. The monitoring of parameters such as oxygen and carbon dioxide concentrations in inspired or expired gases in a patient's airway has become of great importance with advances in medical technology, but the accuracy of the measurement of such parameters can be adversely affected by pressure fluctuations in the test gas caused by pressure fluctuations in the patient airway or by pump elements and the like in the gas sensing equipment itself.

In accordance with the invention, a test gas is drawn into a sensor through a storage capacitor which stores the test gas. Thereafter, a constant pressure alternate gas source is placed in fluid communication with the storage capacitor, isolating the storage capacitor and the sensor from fluctuations in the pressure of the main body of the test gas while a selected parameter of the test gas is being measured. The invention thus provides a simple and effective means for accurately measuring selected parameters of the test gas notwithstanding fluctuations in the pressure of the main body of the test gas.

More particularly, as is shown schematically in FIG. 1, an apparatus according to the invention for measuring a selected parameter of a test gas in isolation from gas pressure fluctuations comprises a sensor 11 operative to measure the selected parameter, a pump 13 downstream from the sensor 11, a storage capacitor 15 upstream from the sensor 11, a constant pressure alternate gas source generally designated 17, and fluid flow control means generally designated 19.

The pump 13 is in fluid communication with the sensor 11 through fluid flow lines 75, 73, cavities 63 and 65, and channel 67. The pump 13 draws the test gas into the sensor 11 for measurement of the selected parameter. The gas ultimately flows out of the sensor 11 into the pump 13 and is then discarded, for example, through an exhaust vent 23.

Figure 2:
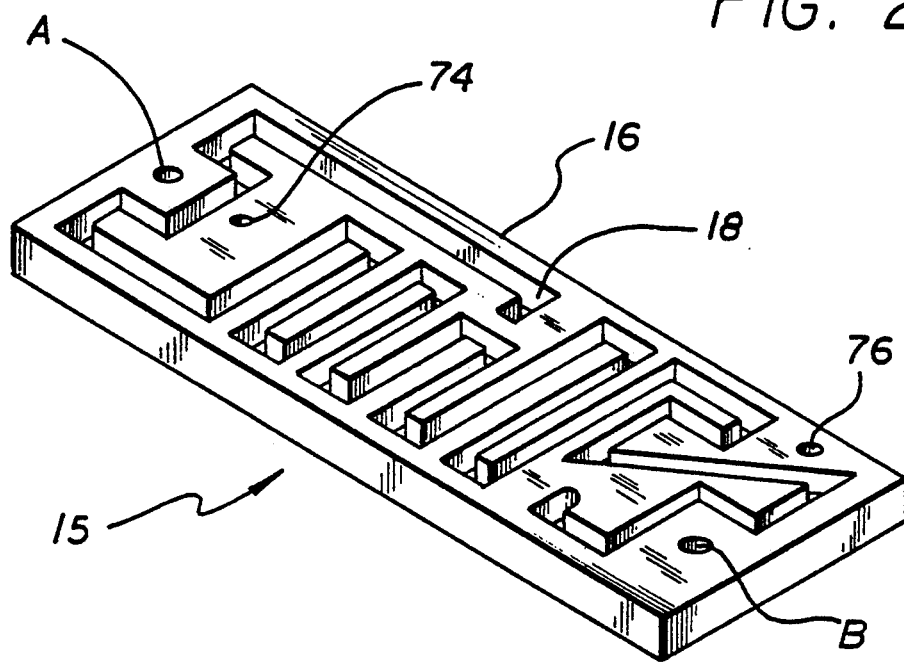
FIG. 2 is a perspective view of the storage capacitor of FIG. 1.
Figure 3:
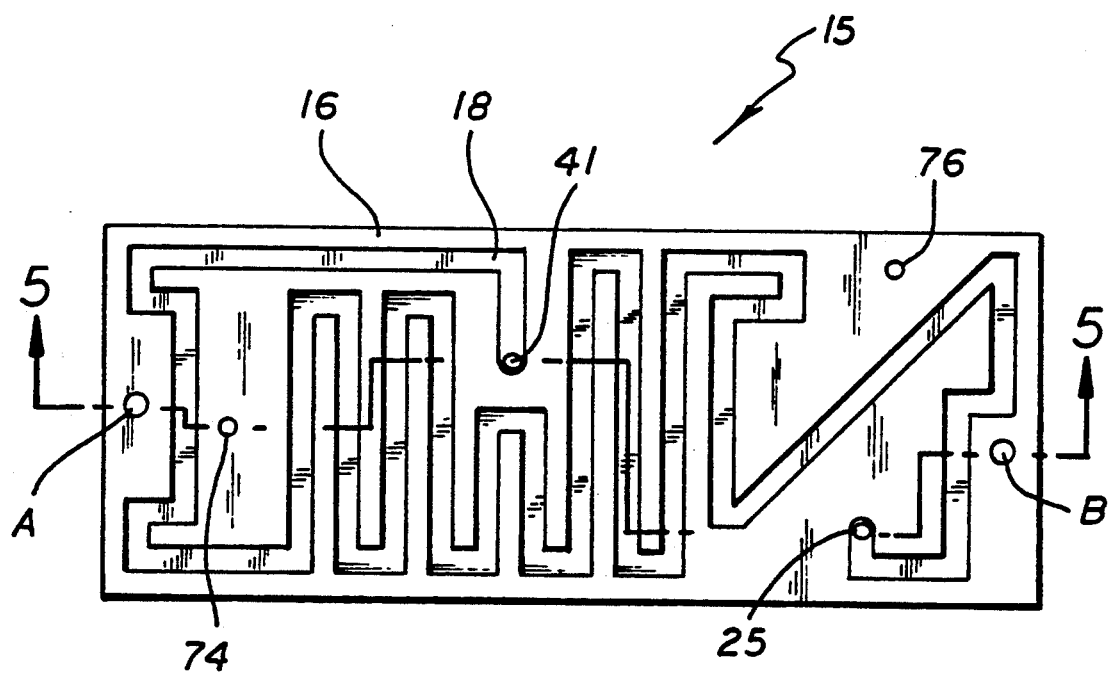
FIG. 3 is a top plan schematic view of the storage capacitor illustrated in FIG. 2.

The storage capacitor 15 in a currently preferred embodiment comprises an enclosed channel 18 formed in a block 16, shown in FIGS. 2 and 3. The enclosed channel is connected in fluid communication with the sensor 11 as shown by a fluid flow line 25 and stores a quantity of gas. The storage capacitor channel 18 preferably comprises an elongated channel or chamber having a length-to-diameter ratio much larger than unity. For example, a channel having a length of about 75 centimeters and a diameter of about 0.5 centimeters has been found to be satisfactory. The storage capacitor 15 is typically sealed by a cover 20 shown in FIG. 5 to form the enclosed channel.

The fluid flow control means 19 opens a first fluid flow path for the test gas into the storage capacitor 15 for a sufficient time to enable the pump 13 to draw the test gas through the storage capacitor 15 into the sensor 11 and thereby to fill the storage capacitor 15 with the gas. Then the flow control means 19 closes the first fluid path and opens a second fluid flow path between the storage capacitor 15 and the alternate gas source 17 and thereby isolates the sensor 11 from any fluctuations in the pressure of the test gas.

The storage capacitor 15 prevents any substantial mixing of the alternate gas with the stored test gas for a sufficient time to enable the sensor 11 to measure the parameter of the test gas under constant pressure conditions without degrading the quality of the measurement. The pressure isolation provided by the storage capacitor 15 permits the test gas to flow continuously through the sensor 11 during the measurement process while preventing pressure fluctuations from interfering with the accuracy of the measurement.

The fluid flow control means 19 preferably comprises a valve such as a solenoid valve 27 having a first inlet 29 in fluid communication with a source such as an airway 31 of the test gas as indicated by a fluid flow line 33, a second inlet 35 in fluid communication with the alternate gas source 17 as indicated by a fluid flow line 37, and an outlet 39 in fluid communication with the storage capacitor 15 as indicated by a fluid flow line 41. The valve 27 opens the first fluid flow path by connecting the outlet 39 to the first inlet 29 as indicated by a first valve connection 43 and opens the second flow path by connecting the outlet 39 to the second inlet 35 as indicated by a second valve connection 45.

The fluid flow control means 19 preferably also includes timing control means 47 such as a microprocessor or the like which selectively applies power to the solenoid valve 27 as indicated by a control line 49 to control the flow of gases into the storage capacitor 15. The timing control means 47 causes the valve 27 to keep the first fluid flow path open long enough to fill the sensor 11 and the storage capacitor 15 with the test gas, then causes the valve 27 to close the first fluid flow path and to open the second fluid flow path to isolate the storage capacitor 15 and the sensor 11 from any pressure fluctuations in the source of the test gas.

The timing control means 47 also controls an output indicator 51 or the like as indicated by a control line 53. The sensor 11 provides a parameter measurement signal to the output indicator 51 as indicated by a control line 55, and the timing control means 47 ensures that an output value is provided only during the time that the pressure of the test gas in the sensor 11 is being held constant. Preferably, the output value is delayed after the second fluid flow path has been opened just long enough for the pressure in the storage capacitor 15 and the sensor 11 to stabilize.

In applications requiring frequent monitoring of a selected parameter of the test gas, the timing control means 47 switches back and forth between the two fluid flow paths, the first path being kept open long enough to ensure that the storage capacitor 15 and the sensor 11 are filled with the test gas and the second path being kept open long enough to ensure that pressures have stabilized before measurements are taken.

The alternate gas source 17 preferably comprises access to the ambient atmosphere, although other sources may be used. The second inlet 35 of the valve 27 is in fluid communication with the ambient atmosphere through the fluid flow line 37 and a vent 57. A flow constrictor 59 in the flow line 37 is preferably used to maintain constant pressure from the alternate gas source 17. In a preferred embodiment the test gas comprises inspired gas in the airway 31 of a patient respirator (not shown).

Figure 4:
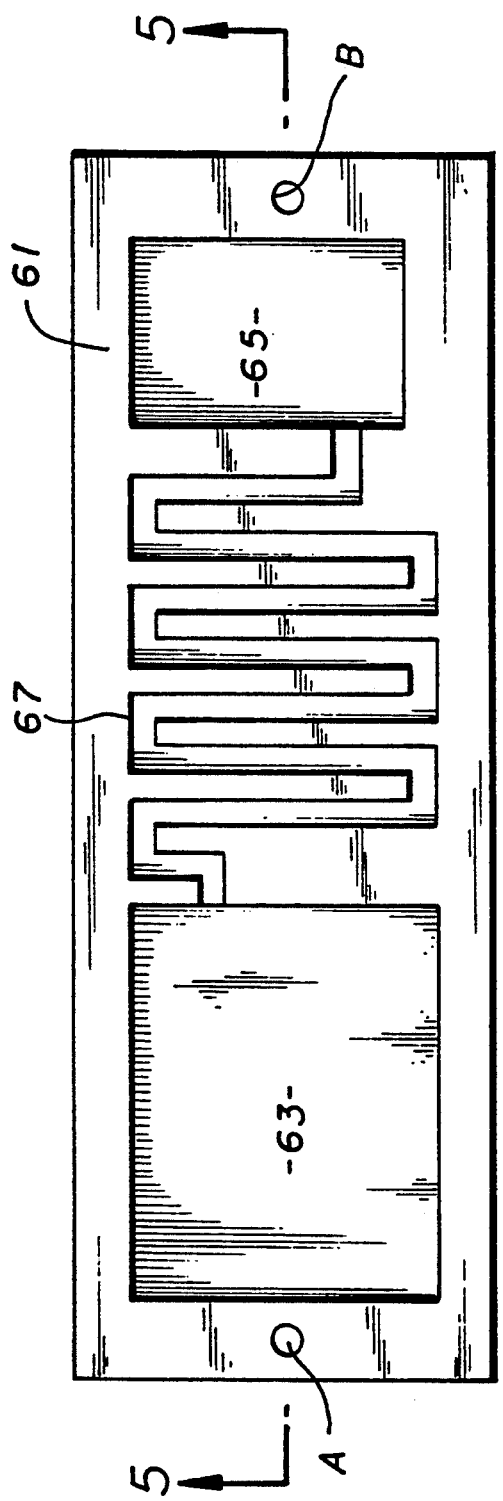
FIG. 4 is a top plan view of the dual chamber pressure damping capacitor of FIG. 1.
Figure 5:
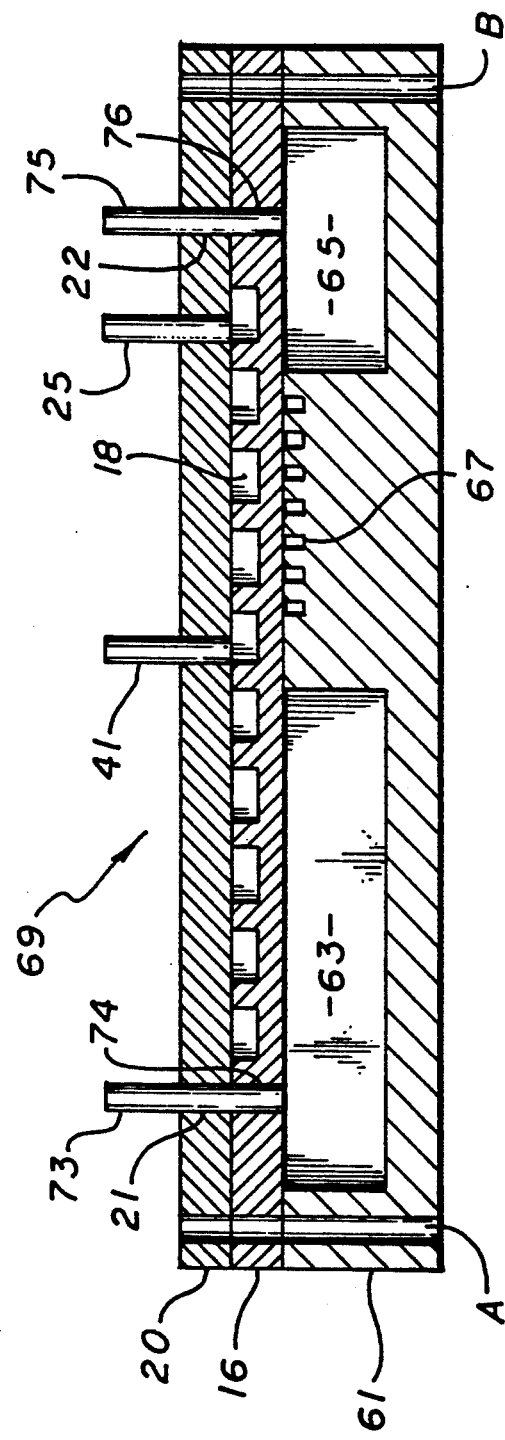
FIG. 5 is a sectional elevational view of the pneumatic block containing the storage capacitor and the dual chamber pressure damping capacitor of FIG. 1.

As shown in FIGS. 4 and 5, in a preferred embodiment, in order to damp out pressure fluctuations generated by the pump or other elements of the gas sensing equipment downstream from the sensor, the portion of the line between the sensor and the pump includes a dual chamber pressure damping capacitor block 61 which includes first and second cavities 63 and 65 and an elongated constrictor channel 67 establishing a resistor fluid flow path between the cavities 63 and 65, the channel 67 also having a length-to-diameter ratio much larger than unity. The cover 20 preferably includes an aperture 21 in connection with line 73 to the pump and outlet 74 in the storage capacitor block 16 from the dual chamber pressure damping capacitor block 61, and an aperture 22 in connection with line 75 from the sensor and inlet 76 in the storage capacitor block 16 to the dual chamber pressure damping capacitor block 61.

The first cavity 63 closest to the pump serves to cushion and damp pressure fluctuations, pressure waves and higher range harmonic vibrations in the gas flowing to the pump by virtue of the relatively larger volume of the first cavity 63 than in the connecting line 73. Lower harmonic pressure fluctuations, pressure waves and vibrations from the pump not filtered out by the first cavity 63 are generally filtered and delayed by the long and narrow constrictor channel 67. Finally any remaining pressure fluctuations, pressure waves and vibrations in the gas in fluid communication with the sensor flowing to the pump are cushioned, damped and filtered by the relatively larger volume of the second cavity 65 in comparison to the narrow constrictor channel and fluid line 75.

The cavities 63 and 65 and the constrictor channel 67 are formed, for example, in an upper surface of a dual chamber pressure damping capacitor block 61. The dual chamber pressure damping capacitor block 61 and the storage capacitor block 16 are preferably joined together to form a pneumatic block 69, allowing vibrations transmitted from the pump to the dual chamber pressure damping capacitor block to be conveyed to the storage capacitor block, to help damp such vibrations with the mass of the storage capacitor block and the gas in the sensing system upstream of the sensor. The cavities 63 and 65 and the constrictor channel of the block 61 are also in this manner covered by the bottom of the storage capacitor block 16, and the two blocks are preferably solvent bonded together to form a gas-tight seal with the adjacent cavities 63 and 65 and the channel 67 to constrain any gas flowing between the cavities 63 and 65 to flow through the channel 67. Holes A and B through the storage capacitor block 16 and the block 61 may also be provided to accommodate bolts or screws for mounting the assembled pneumatic block 69 within the gas parameter measuring apparatus. Fluid communication for a gas to enter and exit the cavities 63 and 65 is provided by means of orifices 73 and 75, respectively, extending through the block 16 and the cover 20. The blocks 16, 61 and the cover 20 may be fabricated from various materials. Acrylic plastic or the like has been found to give satisfactory results.

A method according to the invention of measuring a selected parameter of a test gas in isolation from gas pressure fluctuations by means of apparatus of the kind described above includes the steps of: opening a first fluid flow path for the test gas into a storage capacitor such as the storage capacitor 15; drawing the test gas through the storage capacitor and into a sensor such as the sensor 11 for measurement of the selected parameter, thereby filling the storage capacitor with the test gas; closing the first fluid flow path; opening a second fluid flow path between a constant pressure alternate gas source such as the source 17 and the storage capacitor and thereby isolating the sensor from any fluctuations in the pressure of the test gas; and measuring the selected parameter of the test gas under constant pressure conditions before any substantial mixing of the alternate gas with the test gas stored in the storage capacitor occurs. In one embodiment the step of opening a first fluid flow path comprises opening a fluid flow path between an airway such as the airway 31 of a patient respirator and the storage capacitor.

From the foregoing it will be appreciated that the method and apparatus of the invention provide a way to accurately measure a selected parameter of a gas which is subject to pressure fluctuations by storing the gas in a storage capacitor and then isolating the storage capacitor from the pressure fluctuations for a sufficient time to permit measurement of the selected parameter. The invention is advantageously used, for example, to accomplish the accurate measurement of such parameters as oxygen and carbon dioxide concentration in inspired or expired gases in an airway of a patient respirator.

Although certain specific embodiments of the invention have been described and illustrated, the invention is not to be limited to the specific forms or arrangements of parts so described and illustrated, and various modifications and changes can be made without departing from the scope and spirit of the invention. Within the scope of the appended claims, therefore the invention may be practiced otherwise than as specifically described and illustrated.

What is claimed is:

1. In a system for measuring oxygen concentration of a test gas, the system including a source of the test gas, a sensor having a substantially linear response to said oxygen concentration in a first desired pressure range and a non-linear response to said oxygen concentration in a second pressure range, said sensor being connected in selective fluid communication with and downstream from the source of the test gas for measuring the oxygen concentration of the test gas, and pump means in fluid communication with the sensor to draw the test gas from the source of the test gas into the sensor, an improvement for isolating the sensor from fluctuations in the pressure of the test gas and maintaining the pressure of the test gas substantially in said first desired pressure range for measuring the oxygen concentration, the improvement comprising:

a storage capacitor upstream from the sensor in fluid communication therewith and operative to store a quantity of gas;

a source of an alternate gas having an essentially constant pressure;

fluid flow control means for isolating the storage capacitor and the sensor from any fluctuations in the pressure of the test gas while said oxygen concentration is being measured, said fluid flow control means having a first fluid flow path connectable between said storage capacitor and said source of the test gas, and a second fluid flow path connectable between said storage capacitor and said source of alternate gas, the fluid flow control means being switchable between a first setting opening the first fluid flow path for the test gas into the storage capacitor and a second setting closing said first flow path and opening the second fluid flow path between the storage capacitor and the alternate gas source;

indicator means in electrical communication with said sensor for providing an output signal representing the measurement of the oxygen concentration; and timing control means in electrical communication with said fluid flow control means and said indicator means for controlling said indicator means to provide said output signal only when the pressure of the test gas in the sensor is held constant, said timing means including means for controlling said fluid flow control means to open the first fluid path to fill said storage capacitor and said sensor with said test gas, and to close said first fluid path and open said second fluid flow path when said storage capacitor and said sensor are filled with said test gas to hold the pressure of the test gas constant during measurement of said oxygen concentration.

2. An improvement according to claim 1 wherein the test gas is inspiration gas provided to a patient, and the fluid flow control means comprises a valve defining said first fluid flow path and said second fluid flow path, the valve being operative to alternatively connect the first fluid flow path to said storage capacitor and said source of the test gas and to connect the second fluid flow path to said storage capacitor and said source of alternate gas.

3. An improvement according to claim 1 wherein the alternate gas source comprises the ambient atmosphere.

4. An improvement according to claim 1 wherein the test gas is inspiration gas provided to a patient, and the source of the test gas comprises an airway of a patient respirator.

5. An improvement according to claim 1 wherein the storage capacitor comprises an elongated chamber having a length of approximately 75 centimeters and a cross-sectional dimension of approximately 0.5 centimeters to allow mixing of the test gas in the storage capacitor before the oxygen concentration of the test gas is measured.

6. The improvement of claim 1, further comprising means for damping fluctuations in pressure in said test gas at said sensor due to said pump means downstream from said sensor, said means for damping including a first enlarged chamber connected for fluid communication with said pump means, a second enlarged chamber connected for fluid communication with said sensor, and an elongated constrictor channel for establishing a resistor fluid flow path connected for fluid communication between said first and second enlarged chambers, and wherein said first and second enlarged chambers and said constrictor channel of said damping means are formed in a top surface of a first block member covered by a bottom surface of a second block member, and said storage capacitor is formed in a top surface of said second block member covered by a third block member.

7. The improvement of claim 6, wherein said second block member includes a first pair of orifices therethrough in fluid communication with said first and second enlarged chambers, said third block member includes a second pair of orifices therethrough, said first and second pairs of orifices being aligned to provide a first flow path to said first enlarged chamber and a second flow path to said second enlarged chamber, and said third block member includes a third pair of orifices therethrough to provide a third and fourth flow path to said storage capacitor.

8. Apparatus for measuring oxygen concentration of a test gas obtained from a source under substantially constant pressure conditions, the apparatus comprising:

a sensor operative to measure the oxygen concentration, said sensor having anon-linear response;

pumping means downstream form the sensor and in fluid communication therewith operative to draw the test gas from said source of the test gas into the sensor for measurement of the oxygen concentration;

means for damping fluctuations in pressure in said test gas at said sensor due to said pumping means downstream from said sensor, said means for damping including a first enlarged chamber connected for fluid communication with said pumping means, a second enlarged chamber connected for fluid communication with said sensor, and an elongated constrictor channel for establishing a resistor fluid flow path connected for fluid communication between said first and second enlarged chambers;

a storage capacitor upstream from the sensor and in fluid communication therewith and operative to store a quantity of gas;

a source of an alternate gas having an essentially constant pressure;

fluid flow control means for isolating the storage capacitor and the sensor from any fluctuations in the pressure of the test gas while said oxygen concentration is being measured, said fluid flow control means having a first fluid flow path connectable between said storage capacitor and said source of the test gas, and a second fluid flow path connectable between said storage capacitor and said source of alternate gas, said fluid flow control means being switchable between a first setting opening the first fluid flow path for the test gas into the storage capacitor and a second setting closing said first flow path and opening the second fluid flow path between the storage capacitor and the alternate gas source, the storage capacitor allowing mixing of the test gas in the storage capacitor while the oxygen concentration is not being measured, and preventing any substantial mixing of the alternate gas with the stored test gas for a sufficient time to enable the sensor to measure the oxygen concentration of the test gas under essentially constant pressure conditions;

indicator means in electrical communication with said sensor for providing an output signal representing the measure of the oxygen concentration; and timing control means in electrical communication with said fluid flow control means and said indicator means for controlling said indicator means to provide said output signal only when the pressure of the test gas in the sensor is held constant, said timing means including means for controlling said fluid flow control means to open the first fluid path ti fill said storage capacitor and said sensor with said test gas, and to close said first fluid path and open said second fluid flow path when said storage capacitor and said sensor are filled with said test gas to hold the pressure of the test gas constant during measurement of said oxygen concentration.

9. Apparatus according to claim 8 wherein the fluid flow control means comprises a valve defining said first fluid flow path and said second fluid flow path, the valve being operative to alternatively connect the first fluid flow path to said storage capacitor and said source of the test gas and to connect the second fluid flow path to said storage capacitor and said source of alternate gas.

10. Apparatus according to claim 8 wherein the alternate gas source comprises the ambient atmosphere.

11. Apparatus according to claim 8 wherein the test gas comprises gas in an airway of a patient respirator.

12. Apparatus according to claim 8 wherein the storage capacitor comprises an elongated chamber having a length of about 75 centimeters and a cross-sectional dimension of about 0.5 centimeters to allow mixing of said test gas in said storage capacitor.

13. The apparatus of claim 8, further including first, second and third block members joined together, and wherein said first and second enlarged chambers and said constrictor channel are formed by a channel in an upper surface of said first block member covered by a lower surface of said second block member forming an upper side wall of said first and second chambers and said constrictor channel, and said storage capacitor is formed by a channel in an upper surface of said second block member covered by a lower surface of said third block member forming an upper sidewall of said storage capacitor.

14. The apparatus of claim 13, wherein said second and third block members include first and second aligned pairs of orifices in fluid communication with said first and second enlarged clambers, and said third block member includes a third pair of orifices in fluid communication with said storage capacitor.

* * * * *